United States Patent
Wu

(10) Patent No.: US 8,506,491 B2
(45) Date of Patent: Aug. 13, 2013

(54) SWITCHING DC CONVERTING DEVICE AND PORTABLE SYSTEM FOR ULTRASONIC MEDICAL IMAGING AND DIAGNOSING AND METHOD THEREOF

(75) Inventor: Feng Wu, Wuxi (CN)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 664 days.

(21) Appl. No.: 12/509,157

(22) Filed: Jul. 24, 2009

(65) Prior Publication Data

US 2010/0022885 A1      Jan. 28, 2010

(30) Foreign Application Priority Data

Jul. 24, 2008   (CN) .......................... 2008 1 0134363

(51) Int. Cl.
*A61B 8/00*         (2006.01)

(52) U.S. Cl.
USPC .......................................... 600/459; 327/145

(58) Field of Classification Search
USPC .......................................... 600/459; 327/145
See application file for complete search history.

(56) References Cited

U.S. PATENT DOCUMENTS

| | | | |
|---|---|---|---|
| 4,160,238 A * | 7/1979 | Weckenmann et al. | ........ 340/3.2 |
| 5,795,297 A | 8/1998 | Daigle | |
| 5,957,846 A | 9/1999 | Chiang et al. | |
| 5,964,709 A | 10/1999 | Chiang et al. | |
| 6,106,472 A | 8/2000 | Chiang et al. | |
| 6,530,887 B1 | 3/2003 | Gilbert et al. | |
| 6,869,401 B2 | 3/2005 | Gilbert et al. | |
| 2006/0094960 A1* | 5/2006 | Phung | ........................ 600/437 |
| 2009/0018442 A1* | 1/2009 | Miller et al. | .................. 600/437 |

* cited by examiner

*Primary Examiner* — Jonathan Cwern
(74) *Attorney, Agent, or Firm* — Armstrong Teasdale LLP

(57) ABSTRACT

A switching DC converting device includes a switching DC converter and a synchronous clock circuit. The synchronous clock circuit is used to provide a wobbling synchronous clock input for the switching DC converter, and the central frequency of the wobbling synchronous clock avoids the operating frequency of a circuit powered by the switching DC converter.

18 Claims, 2 Drawing Sheets

SWITCHING DC CONVERTING DEVICE AND PORTABLE SYSTEM FOR ULTRASONIC MEDICAL IMAGING AND DIAGNOSING AND METHOD THEREOF

FIELD OF THE INVENTION

The embodiments described herein relate to a switching DC converter and a portable system for ultrasonic medical imaging and diagnosing using the same, and in particular to a portable system for ultrasonic medical imaging and diagnosing having a Continuous Wave Doppler (CWD) and a Pulsed Wave Doppler (PWD) receiving circuits. Moreover, it also relates to a method for reducing influence of radiation interference noise of the switching DC converter on an ultrasonic receiving circuit (e.g. CWD and PWD receiving circuits) in the portable system for ultrasonic medical imaging and diagnosing.

CROSS REFERENCE TO RELATED APPLICATIONS

This application claims the benefit of Chinese Patent Application No. 200810134363.9 filed Jul. 24, 2008, which is hereby incorporated by reference in its entirety.

BACKGROUND OF THE INVENTION

In a portable system for ultrasonic medical imaging and diagnosing having CWD and PWD functions, CWD and PWD receiving circuits are so sensitive to noise generated by a power supply such that CWD and PWD images are susceptible to interference, so noise is a critical and difficult problem to the portable system for ultrasonic medical imaging and diagnosing. Generally, in a very small space of the portable system for ultrasonic medical imaging and diagnosing, to improve an efficiency of the power supply, an efficient switching DC converter, i.e. a DC-DC converter, is used to realize a power conversion, for example, a reduction from a high voltage (e.g. 20V) to a voltage (e.g. 5V) that is actually needed by a circuit, in order to supply the needed voltage to the circuit of the system. However, the switching DC-DC converter will generate some radiation interference noises (e.g. interference and noise generated by harmonics) while improving the efficiency of the power supply, thereby influencing image quality in the CWD and PWD receiving circuits. The portable system for ultrasonic medical imaging and diagnosing in the prior art either gives no consideration to the influence of the noise of the DC-DC converter on the CWD and PWD images or fails to put forward a good solution to such influence.

BRIEF DESCRIPTION OF THE INVENTION

Embodiments of the invention facilitate reducing influence of radiation interference noise of a switching DC converter on a circuit powered thereby.

Moreover, embodiments of the invention facilitate reducing influence of radiation interference noise of a switching DC converter in a portable system for ultrasonic medical imaging and diagnosing on a system receiving circuit (e.g. CWD and/or PWD receiving circuit, etc.), thereby improving quality of a system image (e.g. CWD and/or PWD image).

According to one aspect of the invention, a switching DC converting device is provided, which comprises a switching DC converter and a synchronous clock circuit. The synchronous clock circuit is used to provide a wobbling synchronous clock input for the switching DC converter. The central frequency of the provided wobbling synchronous clock avoids the operating frequency of a circuit powered by the switching DC converting device, wherein the output frequency of the synchronous clock only needs to be synchronous to the phase of the operating frequency of the system using said switching DC converter device, while the frequencies thereof do not have to be the same.

The switching DC converter device can be used in a portable system for ultrasonic medical imaging and diagnosing, wherein the synchronous clock circuit can be provided in a system controller of the portable system for ultrasonic medical imaging and diagnosing, and the system controller can be implemented by a Field Programmable Gate Array (FPGA).

The circuit powered by the switching DC converting device may include a Continuous Wave Doppler (CWD) receiving circuit and/or a Pulsed Wave Doppler (PWD) receiving circuit, etc.

According to another aspect of the invention, a portable system for ultrasonic medical imaging and diagnosing is provided, which comprises a system controller, a system receiving circuit, a switching DC converter, and a synchronous clock circuit. The synchronous clock circuit is used to provide a wobbling synchronous clock input for the switching DC converter. The central frequency of the wobbling synchronous clock avoids the operating frequency of the system receiving circuit powered by the switching DC converter. The system receiving circuit may include a Continuous Wave Doppler (CWD) receiving circuit and/or a Pulsed Wave Doppler (PWD) receiving circuit, etc. The synchronous clock circuit together with the switching DC converter forms a switching DC converting device. The synchronous clock circuit may be provided in the system controller of the portable system for ultrasonic medical imaging and diagnosing. The system controller and the synchronous clock circuit can be implemented by a FPGA.

According to a further aspect of the invention, there is provided a method for reducing influence of radiation interference noise of a switching DC converter on an ultrasonic receiving circuit in a portable system for ultrasonic medical imaging and diagnosing. Said method is mainly implemented by controlling the synchronous clock input of the switching DC converter so as to cause the synchronous clock to wobble, wherein the central frequency of the wobbling synchronous clock avoids the operating frequency of the ultrasonic receiving circuit in the portable system for ultrasonic medical imaging and diagnosing. Said method is particularly suitable for a portable system for ultrasonic medical imaging and diagnosing that includes a Continuous Wave Doppler (CWD) receiving circuit and/or a Pulsed Wave Doppler (PWD) receiving circuit.

The synchronous clock input of the DC-DC converter is controlled by adding the synchronous clock connected to the DC-DC converter, that is, it inputs a wobbling synchronous clock to the DC-DC converter so as to make a radiation frequency of the DC-DC converter wobble. Since the noise interference of the DC-DC converter is generated by the harmonics thereof in a certain frequency (i.e. the main operating frequency thereof), the wobbling synchronous clock expands the radiation frequency spectrum of the DC-DC converter and disperses the energy at the harmonic frequency locations, thereby reducing the radiation interference noise of the DC-DC converter, improving the noise performance of the portable system for ultrasonic medical imaging and diagnosing, which in turn reduces the interference to the CWD and PWD receiving circuits, and improves the image quality of the PWD and CWD receiving circuits.

In addition, only a very small change is made to circuit design, and it is highly flexible in design so as to be integrated into an existing portable system for ultrasonic medical imaging and diagnosing.

DETAILED DESCRIPTION OF THE INVENTION

The invention will be described below in further detail by way of embodiments, but it is not limited to these embodiments.

Figure 2:
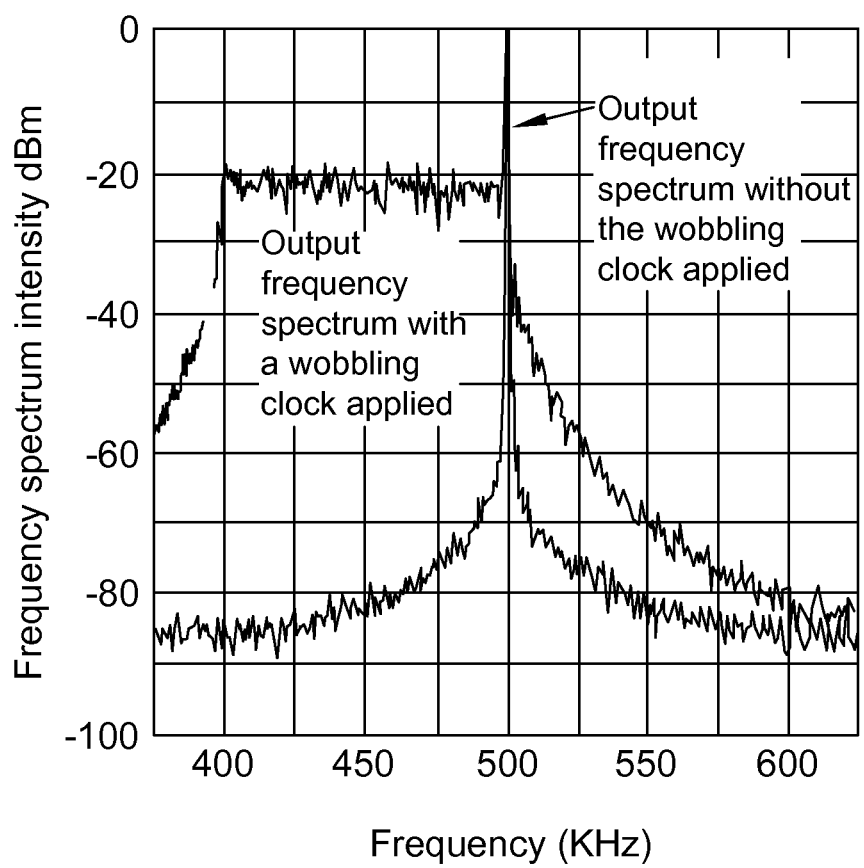
FIG. 2 shows a schematic drawing of a comparison between an output frequency spectrum of a pulse to which a wobbling clock is applied and an output frequency spectrum of the pulse without the wobbling clock applied.

In one embodiment, a switching DC converting device includes a switching DC converter and a synchronous clock circuit providing a specified wobbling synchronous clock input for said switching DC converter, wherein the switching DC converter is the one (DC-DC converter) commonly used in the prior art, and the output frequency of the synchronous clock circuit only needs to be synchronous to the phase of the operating frequency of the system using said switching DC converter device, while the frequencies thereof do not have to be the same. When using such switching DC converting device, the central frequency of the wobbling synchronous clock in the synchronous clock circuit thereof is set to be different from the operating frequency of a circuit powered by the switching DC converting device, thus reducing influence of radiation interference noise of the switching DC converting device on the circuit powered thereby. As shown in FIG. 2, when a wobbling synchronous clock frequency is applied to a pulse, the frequency spectrum thereof is expanded, so a single pulse originally having a very high peak value is expanded to a frequency spectrum band with a reduced peak value. Such switching DC converting device can be used in the existing portable system for ultrasonic medical imaging and diagnosing, in particular in the portable system for ultrasonic medical imaging and diagnosing that includes circuits like CWD and PWD receiving circuits that are susceptible to interference of radiation noise. The synchronous clock circuit in the switching DC converting device may be placed in a controller of the portable system for ultrasonic medical imaging and diagnosing and be formed together with the controller by an FPGA, or it may be provided as a separate component or be provided in the switching DC converter as desired.

Figure 1:
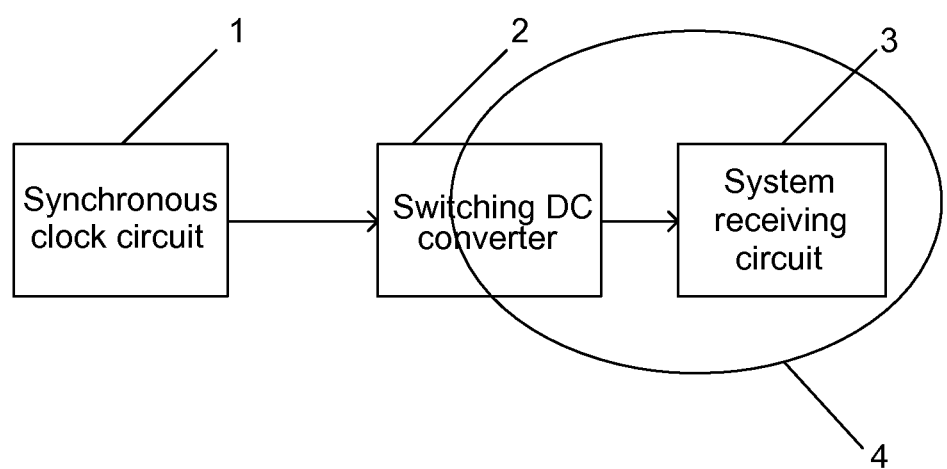
FIG. 1 is a schematic block diagram of an embodiment a portable system for ultrasonic medical imaging and diagnosing.

FIG. 1 is a simple schematic drawing of a switching DC converting device that may be used with a portable system for ultrasonic medical imaging and diagnosing. As shown in FIG. 1, the portable system for ultrasonic medical imaging and diagnosing according to the present invention comprises a synchronous clock circuit 1, a switching DC converter 2 (i.e. a DC-DC converter), and a system receiving circuit 3 powered by the DC-DC converter 2. The system receiving circuit 3 includes CWD and PWD receiving circuits, etc. The synchronous clock circuit 1 can be provided in a system controller of the portable system for ultrasonic medical imaging and diagnosing, and the output frequency thereof only needs to be synchronous to the phase of the operating frequency of the portable system for ultrasonic medical imaging and diagnosing, while the frequencies thereof do not have to be the same. The synchronous clock circuit 1 is used to provide a specified wobbling synchronous clock input for the DC-DC converter 2. The central frequency of the provided wobbling synchronous clock avoids the operating frequency of the system receiving circuit (e.g. CWD and PWD receiving circuits), wherein the system controller and the synchronous clock circuit 1 provided therein can be implemented by an FPGA.

Alternatively, in the portable system for ultrasonic medical imaging and diagnosing, the synchronous clock circuit 1 together with the switching DC converter 2 may form a switching DC converting device.

As shown in FIG. 1, the switching DC converter 2 has a radiation interference area 4 which covers most areas of the system receiving circuit 3. That is to say, the system receiving circuit 3 in the radiation interference area 4 is susceptible to radiation interference noise of the switching DC converter 2. In the present invention, the frequency provided by the synchronous clock circuit 1 is wobbling to expand the frequency spectrum of the DC-DC converter 2, so the output frequency spectrum becomes flat, similarly as shown in FIG. 2. In this way, when the DC-DC converter 2 provides the needed power supply for the ultrasonic receiving circuit (e.g. the CWD and PWD receiving circuits) of the portable system for ultrasonic medical imaging and diagnosing, the energy at harmonic frequency locations of the operating frequency thereof is dispersed, thus reducing influence of noise generated by the harmonics thereof on the output of the ultrasonic receiving circuit (e.g. the CWD and PWD receiving circuits) of the system, and ensuring a better quality of the image output from the ultrasonic receiving circuit (e.g. the CWD and PWD receiving circuits) of the system.

In addition, the present invention also provides a method for reducing influence of radiation interference noise of a switching DC converter on an ultrasonic receiving circuit in a portable system for ultrasonic medical imaging and diagnosing. Said method is mainly implemented by controlling a synchronous clock input of the switching DC converter, i.e. inputting a wobbling synchronous clock to the switching DC converter, to expand the output frequency spectrum of the switching DC converter, wherein the central frequency of the wobbling synchronous clock avoids the operating frequency of the ultrasonic receiving circuit in the portable system for ultrasonic medical imaging and diagnosing. Said method is particularly suitable for a portable system for ultrasonic medical imaging and diagnosing including a Continuous Wave Doppler (CWD) receiving circuit and/or a Pulsed Wave Doppler (PWD) receiving circuit. Of course, said method of the invention can also be used in any other circuit or system that is sensitive to the radiation interference noise of the switching DC converter, while it is not limited to be used only in the above-mentioned portable system for ultrasonic medical imaging and diagnosing.

The above are only specific embodiments of the invention. It shall be pointed out that many modifications, alterations and variations can be made by those skilled in the art without departing from the spirit of the present invention. Accordingly, all such modifications, alterations and variations shall be deemed as falling within the protection scope of this application.

What is claimed is:
1. A switching DC converting device comprising:
   a switching DC converter; and
   a synchronous clock circuit configured to provide a wobbling synchronous clock input for the switching DC converter, wherein a central frequency of the wobbling synchronous clock provided by the synchronous clock circuit is synchronous to a phase of and different than an operating frequency of a circuit powered by the switching DC converting device.

2. The switching DC converting device according to claim 1, which is used in a portable system for ultrasonic medical imaging and diagnosing.

3. The switching DC converting device according to claim 2, wherein the synchronous clock circuit is provided in a system controller of the portable system for ultrasonic medical imaging and diagnosing.

4. The switching DC converting device according to claim 3, wherein the system controller and the synchronous clock circuit are implemented by a Field Programmable Gate Array.

5. The switching DC converting device according to claim 2, wherein the circuit powered by the switching DC converting device comprises at least one of a Continuous Wave Doppler receiving circuit and a Pulsed Wave Doppler receiving circuit.

6. The switching DC converting device according to claim 1, wherein the circuit powered by the switching DC converting device comprises at least one of a Continuous Wave Doppler receiving circuit and a Pulsed Wave Doppler receiving circuit.

7. The switching DC converting device according to claim 1, wherein the central frequency of the wobbling synchronous clock is synchronous with the operating frequency of the circuit powered by the switching DC converting device.

8. A portable system for ultrasonic medical imaging and diagnosing, said portable system comprising:
   a system controller;
   a system receiving circuit;
   a switching DC converter; and
   a synchronous clock circuit configured to provide a wobbling synchronous clock input for the switching DC converter, wherein a central frequency of the wobbling synchronous clock is synchronous to a phase of and different than an operating frequency of the system receiving circuit powered by the switching DC converter.

9. The portable system for ultrasonic medical imaging and diagnosing according to claim 8, wherein the system receiving circuit comprises at least one of a Continuous Wave Doppler receiving circuit and a Pulsed Wave Doppler receiving circuit.

10. The portable system for ultrasonic medical imaging and diagnosing according to claim 9, wherein the synchronous clock circuit is provided in the system controller of the portable system for ultrasonic medical imaging and diagnosing.

11. The portable system for ultrasonic medical imaging and diagnosing according to claim 8, wherein the synchronous clock circuit together with the switching DC converter forms a switching DC converting device.

12. The portable system for ultrasonic medical imaging and diagnosing according to claim 11, wherein the synchronous clock circuit is provided in the system controller of the portable system for ultrasonic medical imaging and diagnosing.

13. The portable system for ultrasonic medical imaging and diagnosing according to claim 8, wherein the synchronous clock circuit is provided in the system controller of the portable system for ultrasonic medical imaging and diagnosing.

14. The portable system for ultrasonic medical imaging and diagnosing according to claim 13, wherein the system controller and the synchronous clock circuit are implemented by a Field Programmable Gate Array.

15. The portable system for ultrasonic medical imaging and diagnosing according to claim 8, wherein the central frequency of the wobbling synchronous clock is synchronous with the operating frequency of the system receiving circuit.

16. A method for reducing influence of radiation interference noise of a switching DC converter on an ultrasonic receiving circuit in a portable system for ultrasonic medical imaging and diagnosing, said method comprising:
   inputting a wobbling synchronous clock to the switching DC converter; and
   operating the wobbling synchronous clock at a central frequency that is synchronous to a phase of and different than an operating frequency of the ultrasonic receiving circuit in the portable system for ultrasonic medical imaging and diagnosing.

17. The method according to claim 16, wherein the ultrasonic receiving circuit in the portable system for ultrasonic medical imaging and diagnosing includes at least one of a Continuous Wave Doppler receiving circuit and a Pulsed Wave Doppler receiving circuit.

18. The method according to claim 16, wherein the central frequency of the wobbling synchronous clock is synchronous with the operating frequency of the ultrasonic receiving circuit.

* * * * *